(12) United States Patent
Castillo et al.

(10) Patent No.: US 10,876,090 B2
(45) Date of Patent: Dec. 29, 2020

(54) CELL GROWTH MATRIX

(71) Applicant: UNIVERCELLS NV, Gosselies (BE)

(72) Inventors: José Castillo, Brussels (BE); Bastien Mairesse, Uccle (BE); Quentin Vanwalleghem, Uccle (BE)

(73) Assignee: UNIVERCELLS TECHNOLOGIES S.A., Nivelles (BE)

( * ) Notice: Subject to any disclaimer, the term of this patent is extended or adjusted under 35 U.S.C. 154(b) by 0 days.

(21) Appl. No.: 15/938,800

(22) Filed: Mar. 28, 2018

(65) Prior Publication Data

US 2018/0282678 A1     Oct. 4, 2018

Related U.S. Application Data

(63) Continuation of application No. PCT/EP2017/078775, filed on Nov. 9, 2017.

(30) Foreign Application Priority Data

Nov. 9, 2016   (BE) .................................. 2016/5839

(51) Int. Cl.
*C12M 1/12* (2006.01)
*C12M 3/00* (2006.01)
(Continued)

(52) U.S. Cl.
CPC .............. *C12M 25/14* (2013.01); *C12M 1/18* (2013.01); *C12M 23/06* (2013.01); *C12M 23/22* (2013.01); *C12M 23/28* (2013.01); *C12M 23/44* (2013.01); *C12M 25/02* (2013.01); *C12M 25/06* (2013.01); *C12M 25/16* (2013.01); *C12M 41/46* (2013.01); *C12N 5/0068* (2013.01); *C12N 5/06* (2013.01);
(Continued)

(58) Field of Classification Search
CPC ...... C12M 23/44; C12M 25/16; C12M 25/06; C12M 25/02; C12M 25/14; C12M 23/06; C12M 1/18; C12M 23/28; C12M 41/46; C12M 23/22; C12N 5/0075; C12N 5/06; C12N 2535/00
See application file for complete search history.

(56) References Cited

U.S. PATENT DOCUMENTS 3,853,712 A    12/1974    House et al.
3,941,661 A     3/1976    Noteboom
(Continued)

FOREIGN PATENT DOCUMENTS

CA    1147679 A     6/1983
EP    0300666 A1    1/1989
(Continued)

OTHER PUBLICATIONS

Lambrechts T et al.; "Evaluation of a monitored muliplate bioreactor for large-scale expansion of human periosteum derived stem cells for bone tissue engineering applications"; Biochemical Engineering Journal, Elsevier, Amsterdam, NL, vol. 108, Jul. 31, 2015, pp. 58-68, XP029436612, ISSn: 1369-703X.
(Continued)

*Primary Examiner* — Gautam Prakash

(57) ABSTRACT

The invention provides a structured cell growth matrix or assembly comprising a one or more spacer layers and one or more cell immobilization layers. The invention further provides a bioreactor comprising said matrix or assembly.

19 Claims, 6 Drawing Sheets

(51) Int. Cl.
- *C12N 5/00* (2006.01)
- *C12M 1/18* (2006.01)
- *C12M 1/00* (2006.01)
- *C12M 1/34* (2006.01)
- *C12N 5/07* (2010.01)

(52) U.S. Cl.
CPC ...... *C12N 2533/90* (2013.01); *C12N 2535/00* (2013.01)

(56) References Cited

U.S. PATENT DOCUMENTS

| | | |
|---|---|---|
| 3,948,732 A | 4/1976 | Haddad et al. |
| 4,144,126 A | 3/1979 | Burbidge |
| 4,546,083 A | 10/1985 | Meyers et al. |
| 4,789,634 A | 12/1988 | Muller-Lierheim et al. |
| 4,861,714 A | 8/1989 | Dean, Jr. et al. |
| 4,937,196 A | 6/1990 | Wrasidlo et al. |
| 5,059,654 A | 10/1991 | Hou et al. |
| 5,079,168 A | 1/1992 | Amiot |
| 5,266,476 A * | 11/1993 | Sussman et al. .... C12N 5/0068 435/179 |
| 5,270,207 A | 12/1993 | Matsumura et al. |
| 5,563,069 A | 10/1996 | Yang |
| 6,245,557 B1 | 6/2001 | Fouts et al. |
| 6,593,136 B1 | 7/2003 | Geiss |
| 6,979,308 B1 | 12/2005 | MacDonald et al. |
| 8,435,781 B2 | 5/2013 | Kodama |
| 9,226,494 B2 | 1/2016 | Chang et al. |
| 2008/0206735 A1 | 8/2008 | Asgari |
| 2010/0075293 A1 | 3/2010 | Chang et al. |
| 2011/0281343 A1 | 11/2011 | Gay |
| 2013/0071872 A1 | 3/2013 | Ho et al. |
| 2014/0193901 A1 | 7/2014 | Lee et al. |
| 2017/0166859 A1 | 6/2017 | Wang et al. |
| 2017/0333815 A1 | 11/2017 | Kompala |
| 2018/0282678 A1 | 10/2018 | Castillo et al. |

FOREIGN PATENT DOCUMENTS

| | | |
|---|---|---|
| GB | 1376131 A | 12/1974 |
| JP | 2001120255 A | 5/2001 |
| WO | 98050522 A1 | 11/1998 |
| WO | WO2011141512 A2 | 11/2011 |

OTHER PUBLICATIONS

English Translation of JP2001120255A dated May 8, 2001.

* cited by examiner

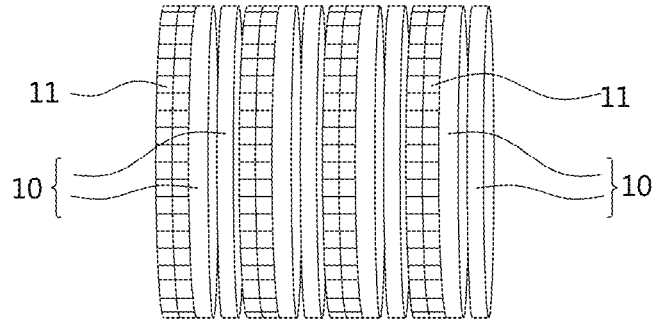
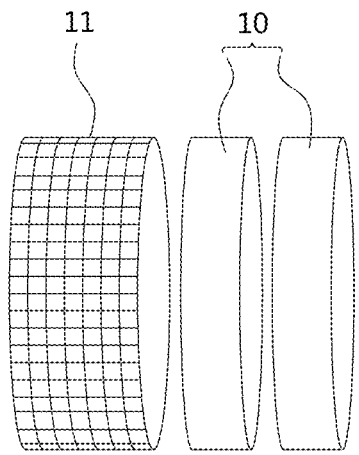
FIG. 2A  FIG. 2B
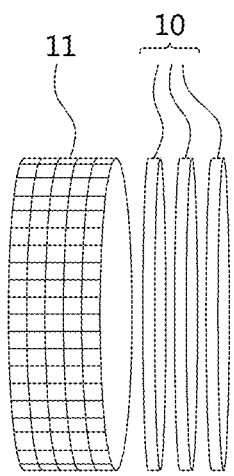
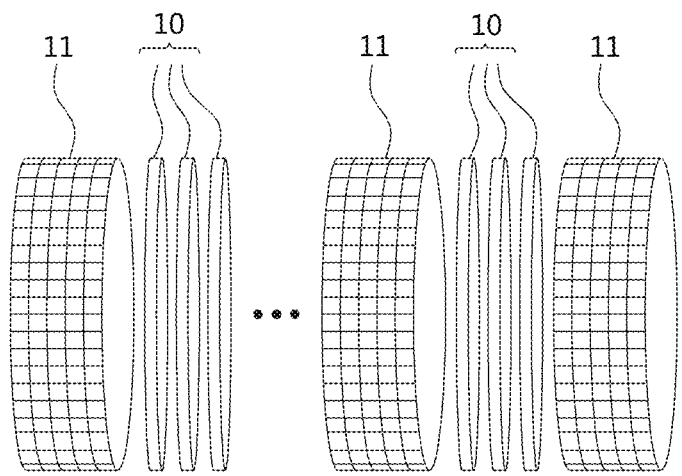
FIG. 2C  FIG. 2D

CELL GROWTH MATRIX

International Application PCT/EP2017/078775, to which this claims priority under 35 USC 120, contains a certified copy of BE 2016/5839.

TECHNICAL FIELD

The present invention concerns cell growth matrix, in particular a structured, high density cell growth matrix. The invention further concerns the use of the matrix for growing cells and a bioreactor comprising said matrix.

BACKGROUND

The techniques to culture cells such as eukaryotic cells, animal cells, mammalian cells and/or tissue are difficult and complex since these cells are delicate and have nutrient and oxygen requirements during growth which are complex and difficult to maintain. Given the increasing need to culture cells in large quantities, bioreactors and culturing devices have become an important tool in research and in the production of cells for producing active proteins and/or antibodies and/or any cell by-products.

The bioreactors of the prior art comprise non-structured cell growth matrixes and are provided with internal or external circulation mechanisms for cell culture medium circulation. The cell growth matrixes generally comprise carriers which can have the form of beads with regular or irregular structure, or may comprise woven or non-woven microfibers of a polymer or any other material compatible with cell growth. The carriers can have a variety of forms and dimensions.

Several drawbacks can be attributed to the known bioreactors and their non-structured cell growth matrixes. The reproducibility lack of volumetric homogeneity of growth matrixes during their packing, and their movement and redistribution over time under the influence of the culture medium flow can lead to unreproducible cell culture environment and very different micro-environments in different portions of the bioreactor. The carriers might gather in a given area inside the bioreactor thereby considerably lowering homogeneity during cell culture. Consequently, part of the cultured cells will have very limited or no access to the culture medium and/or oxygen supply, which results in different cells metabolism, differences in product quality, even the death of said cells and a low cells production rate. Additionally, the non-homogenous matrixes are difficult to produce and to pack given the variable sizes and shapes of the carriers which might stick to each other. Another drawback of the cell growth matrixes of the prior art is that their cell culture surface cannot be determined with precision. Lastly, packing the carriers in the bioreactor is laborious and thus costly.

U.S. Pat. No. 3,948,732 describes an assembly which includes a spiral-wound tubular chamber unit through which culture media and cells travel within the chamber and about the center of the spiral and adhere to the inside wall of the chamber. The assembly includes a spacer member provided with spaced projecting support members which is interleaved with the tubular chamber unit. These projecting members are intended to facilitate gas flow through the cross section of the spiral assembly in an axial direction. At no time does the spacer member come into contact with any of the cells or cell culture medium within the tube much less provide a path for the cells in any way.

It is the aim of the present invention to provide a cell growth matrix and a bioreactor comprising said matrix which overcome at least part of the above mentioned drawbacks. By preference, the cell growth matrix should provide for a large cell growth surface within a small volume while still allowing circulation of medium and cells. Pressure drops within the system should be avoided as this is counterproductive to certain cell viability. Reproducibility and homogeneity should be enhanced while maintaining manual operation and cost at an absolute minimum. A tortuous path for cells and cell culture media to travel is needed in conjunction with a spacer layer that facilitates that path along and parallel to the spacer layer and cell immobilization layers.

SUMMARY OF THE INVENTION

In a first aspect, the present invention provides a cell growth matrix assembly or structured cell growth matrix.

In a second aspect, the present invention provides for the use of the cell growth matrix assembly or matrix according to any embodiment of the invention for growing cells.

In a third aspect, the present invention provides a bioreactor comprising a cell growth matrix assembly or matrix according to any embodiment of the invention.

The cell growth matrix assembly or matrix of the current invention present several advantages compared to those known in the prior art. By making use of a structured assembly, variability during the cell growth process is omitted or minimalized. The cell culture surface can be easily and accurately determined thanks to the known cell culture surface and the number of the immobilization layers. The cell culture surface to be placed inside a bioreactor can also be easily adapted without modification of the matrix and/or the bioreactor design.

The matrix provides improved and organized cell and cell culture medium flow inside a bioreactor.

Furthermore, the structured cell growth matrix provides efficient packing inside a bioreactor thereby optimizing the use of the inner space and increasing the cell growth surface inside said bioreactor. The matrix thereby provides high cell density culture surface. Moreover, thanks to the structured design of the matrix, consistent and reproducible production of bioreactors containing said matrix is facilitated.

DESCRIPTION OF FIGURES

FIGS. 2A, 2B, 2C and 2D shows non-limitative examples of a matrix assembly according to embodiments of the current invention.

DETAILED DESCRIPTION OF THE INVENTION

Figure 1A:
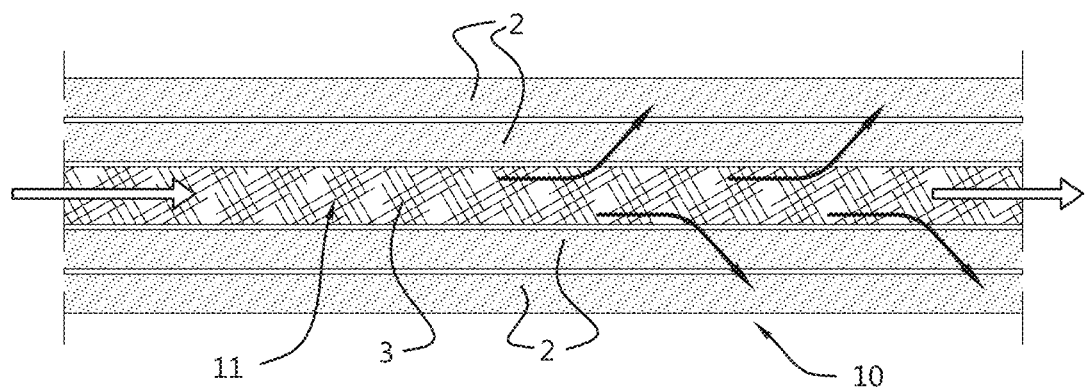
FIGS. 1A and 1B show cross sectional views of portions of a matrix assembly according to two embodiments of the current invention.

The present invention concerns a cell growth matrix assembly, the use of the latter for cell growth and a bioreactor comprising said matrix assembly.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The terms assembly, matrix assembly and matrix are used interchangeable throughout the text.

In a first aspect, the current invention provides for a cell growth matrix assembly, which comprises one or more cell immobilization layers having a surface which allows cells to adhere and grow upon and forming a cell immobilization section. Adjacent to these cell immobilization layers are one or more spacer layers, including a structure which forms a spacer section allowing passage of cells and medium through an open but tortuous path whereby the structure or nature of the spacer layers is chosen such that the spacer layers create a tortuous, open path for cells and culture media to travel in parallel to the surface of said spacer and immobilization layers. The tortuous path or channel formed by the spacer section creates turbulence which facilitates cell and cell medium incursion into the immobilization layers.

Said cell immobilization layers will define a cell immobilization section, whereas said spacer layers define a spacer section.

In further or alternative embodiment, the present invention provides a structured cell growth matrix comprising one or more spacer sections and one or more cell immobilization sections. Each spacer section comprises at least one spacer layer and each cell immobilization section comprises at least one cell immobilization layer, wherein the thickness ratio of the immobilization section to the spacer section is at least 0.1 and the thickness of the spacer section is at least 0.1 mm. In an embodiment, the spacer section includes a structure that provides a tortuous path or channel for cells to travel along the layers.

For the purpose of the current invention, a tortuous path is to be understood as a path with directional components that vary from and along the general path.

The matrix assembly is designed such that it allows fluid and cells to flow axially along the surfaces of the spacer layer and cell immobilization layer in a stationary bioreactor, or in the case of a rotating bioreactor, tangentially along the surfaces of both layers. The structure of the spacer layers should be thus chosen that it creates a tortuous, yet open path in between immobilization layers, thereby creating turbulence. This turbulence will drive cells and medium into the immobilization layers.

It will be understood by the skilled person that such tortuous path spacer could be achieved by multiple ways, all readily known in the art. In one embodiment, the spacer layer is comprised of a bearing structure or spherical, near-spherical or egg-shaped objects such as beads, packed as a three-dimensional structure on top of each other (see FIG. 1B). A bearing structure is to be understood as a structure formed of balls or spheres optionally fixed to a surface support, which form a tortuous path through which fluid may flow.

In another embodiment, the spacer layer may be a mesh or comprises a mesh structure. For the purpose of the current invention, mesh structure or mesh is to be understood as a structure comprising a network or web-like pattern of filament, wire or thread, said network defines pores, openings or perforations formed of a three dimensional weave. Examples of mesh structures are given in FIGS. 4A to 4D. It will be understood that these cannot be seen as limitative to the current invention.

The cell growth matrix assembly or matrix according to the current invention provides for a substrate that allows high density cell growth. By preference, a high cell density bioreactor allows for the maximum of cell growth surface in a minimum of volume. The design of the current cell growth matrix assembly is optimized to meet these demands. By providing a spacer section adjacent to the immobilization section, cell and medium flow is ensured. These spacer sections promote turbulence and allow essentially tangential flow in between cell adherence sections, in addition to random perpendicular flow through the immobilization layers. This increases cells adherence to the immobilization layers of the immobilization sections.

Additionally, the cells are more homogenously distributed inside the bioreactor thanks to the spacer sections which provide space for cell movement until adherence, and which prevents the immobilization sections from acting as filters. The spacer further allows improved removal of toxic metabolites by providing space for the movement of said metabolites.

The spacer section further allows better distribution of the culture medium and thereby of the nutrients inside the bioreactor. All cells inside the bioreactor are equally provided with culture medium. Given the structured design of the matrix, preferential culture medium route will not be created inside a bioreactor. This is an improvement over the non-structured matrixes of the prior art, which generate preferential culture medium routes when used in a bioreactor as the non-structured carriers move under the influence of the culture medium flow. The result is a non-homogeneous cell distribution.

In order to ensure a minimal of pressure drop and volume loss, the spacer section is comprised of a structure including a tortuous path for cell and fluid flow. In one embodiment, the structure is a mesh. By using a mesh structure for spacer section, the thickness of the physical barrier is kept to an absolute minimum thereby ensuring constant pressure and yet still allowing sufficient space between the neighboring immobilization sections.

In an embodiment the structure or mesh size of the spacer layer will be between 0.05 mm to 5 mm. The choice of the structure or mesh size is important as it again influences the balance between providing a sufficient barrier between the immobilization sections thereby allowing cell and medium passage, whilst ensuring adequate pressure in the system and achieving a high cell density. The openings in the mesh or grid can be of any shape, such as round, elliptical, square, or rectangular. In an embodiment, the size of the openings is at least 0.05 mm, at least 0.06 mm, at least 0.08 mm, at least 0.1 mm, at least 0.15 mm, at least 0.2 mm or at least 0.25 mm. In another or further embodiment, the size of the openings is at most 5 mm, at most 4.5 mm, at most 4 mm, at most 3.5 mm, at most 3 mm or any value comprised in between the aforementioned values.

It will be understood that the thickness of the spacer section, which is built from one or more spacer layers will have an impact on the functioning of the matrix assembly. In an embodiment the thickness of the spacer section is at least 0.1 mm, more preferably between 0.1 mm and 5 mm, more preferably between 0.2 mm and 1 mm. In an embodiment, the thickness of the spacer section is between 0.25 and 0.6 mm, such as 0.4 mm or 0.5 mm.

In an embodiment the thickness in mm of the spacer section is at least 0.1, at least 0.2, at least 0.3, at least 0.4, at least 0.5, at least 0.6, at least 0.7, at least 0.8, at least 0.9, at least 1, at least 1.1, at least 1.2, at least 1.3, at least 1.4, at least 1.5, at least 1.6, at least 1.7, at least 1.8, at least 1.9, at least 2, at least 2.1, at least 2.2, at least 2.3, at least 2.4, at least 2.5, at least 2.6, at least 2.7, at least 2.8, at least 2.9, at least 3, at least 3.1, at least 3.2, at least 3.4, at least 3.5, at least 3.6, at least 3.7, at least 3.8, at least 3.9, at least 4, at least 4.1, at least 4.2, at least 4.3, at least 4.4, at least 4.5, at least 4.6, at least 4.7, at least 4.8, at least 4.9, at least 5, at least 5.5, at least 6, at least 6.5, at least 7, at least 7.5, at least 8, at least 8.5, at least 9, at least 9.5, at least 10 or any value comprised between the aforementioned values.

In a further or alternative embodiment, the thickness in mm of the spacer section is at most 1000, at most 950, at most 900, at most 850, at most 800, at most 750, at most 700, at most 650, at most 600, at most 550, at most 500, at most 450, at most 400, at most 350, at most 300, at most 250, at most 200, at most 190, at most 180, at most 170, at most 160, at most 150, at most 140, at most 130, at most 120, at most 110, at most 100, at most 95, at most 90, at most 85, at most 80, at most 75, at most 70, at most 65, at most 60, at most 55, at most 50, at most 45, at most 40, at most 35, at most 30 at most 25, at most 20, at most 15, at most 12 or any value comprised between the aforementioned values.

The thickness of the cell immobilization section will equally be of importance to the functioning of the system. A cell immobilization section which is too thick will result in a poorly populated area, whereas a section which is too thin will have a negative impact on the available cell growth surface, again negatively influencing cell growth. By preference, the thickness of the immobilization section will be between 0.1 mm and 15 mm, more preferably between 0.1 mm and 10 mm, even more preferably between 0.1 and 5 mm, or between 0.1 mm and 1 mm.

There is a need for a balance between sufficient cell and medium flow between the cell growth surfaces and a sufficiently large cell surface for cell growth. The inventors of the current invention have found that ideally, the ratio between the thickness of the cell immobilization section to the spacer section should be at least 0.1, and more preferably between 0.1 and 5, even more preferably between 0.1 and 2, such as e.g. 1:1. As such, the needs of the system are met.

In an embodiment, the thickness ratio of the immobilization section to the spacer section is at least 0.1, at least 0.2, at least 0.3, at least 0.4, at least 0.5, at least 0.6, at least 0.7, at least 0.8, at least 0.9, at least 1, at least 1.1, at least 1.2, at least 1.3, at least 1.4, at least 1.5, at least 1.6, at least 1.7, at least 1.8, at least 1.9, at least 2, at least 2.1, at least 2.2, at least 2.3, at least 2.4, at least 2.5, at least 2.6, at least 2.7, at least 2.8, at least 2.9, at least 3, at least 4, at least 5, at least 6, at least 7, at least 8, at least 9, at least 10 or any value comprised between the aforementioned values.

In a further or alternative embodiment, the thickness ratio of the immobilization section to the spacer section is at most 50, at most 45, at most 40, at most 35, at most 30, at most 25, at most 20, at most 19, at most 18, at most 17, at most 16, at most 15, at most 14, at most 13, at most 12, at most 11 or any value comprised between the aforementioned values.

The spacer layers and/or the cell immobilization layers which make up respectively the spacer section and the immobilization section in the matrix assembly are preferably made of a biocompatible polymer selected from polyester, polyethylene, polypropylene, polyamide, plasma treated polyethylene, plasma treated polyester, plasma treated polypropylene or plasma treated polyamide. Said layers can be hydrophilic or hydrophobic. The cell immobilization layers are preferably hydrophilic.

The thickness of both layers will advantageously be between 0.05 mm and 3 mm, more preferably between 0.1 and 2 mm or between 0.1 and 1 mm.

Suitable material for the cell immobilization layer may be a woven or nonwoven material. By preference, a nonwoven material is used. A nonwoven, contrary to a woven material, is a fabric which is not created by weaving or knitting and does not require converting the fibers to yarn. Nonwovens are broadly defined as sheet or web structures bonded together by entangling fiber or filaments (and by perforating films) mechanically, thermally or chemically. The nature of the nonwoven material used in the current application may be of any origin, either comprising of natural fibers or synthetic fibers. By preference, the nonwoven is made of a polymer, such as polyester or polypropylene. The cell immobilization layers used in the current invention may be chosen from a polyethyleentereftalate nonwoven. The nonwoven material may be plasma treated to enhance cell adherence and flow.

The spacer layers may consist of a (biocompatible) polymer with mesh size as described above. In one embodiment, the spacer layer is a synthetic woven fabric or structure. In another embodiment, the spacer layer is a bearing structure. Such structure may be produced from a biopolymer (e.g. alginate). Other suitable material for this purpose is silica, polystyrene, agarose, styrene divinylbenzene, polyacrylonitrile or latex.

The spacer layer may be gamma irradiated in order to reduce bioburden.

The design of the matrix assembly can take many forms depending on the application and type of bioreactor.

In an embodiment of the current invention, the immobilization section and spacer section are alternately positioned. Alternately positioned means that each spacer section is followed by a cell immobilization section which is itself followed by a spacer section. The alternately positioned sections may alternate in vertical position as shown in the figures (see further) or in a horizontal position according to the use of the matrix and/or to the bioreactor in which the matrix will be introduced.

In this embodiment, one or more layers of cell immobilization layers are superimposed on one or more spacer layers (or vice versa). This configuration may be repeated several times if deemed required in order creating a stack of several immobilization and spacer sections. Ideally, the end configuration may comprise between 1 and 500 alternations of the above described layering. The stacked layers may be positioned in a frame or cassette or sealed/connected at their circumference. In another embodiment, the achieved stack can be rolled around an axis or core to achieve a spiral configuration.

The amount of layers used in both the immobilization section and spacer section can be chosen based on the application, characteristics of the layers (dimensions, size, etc.) and desired result. Hence, the amount of layers within either immobilization section or spacer section may be between 1 and 20, more preferably between 1 and 10, even more preferably between 1 and 5.

As mentioned, the presence of the spacer sections creates space inside the matrix through which the culture medium flows. This provides improved circulation of the culture medium through the matrix thereby reaching all cultured cells. This effect is even more enhanced in the embodiment wherein the spacer section comprises one spacer layer and the immobilization section comprises two immobilization layers. The culture medium flowing inside the matrix via the spacer sections is tangentially oriented with respect to the cell immobilization sections.

The spacer sections improve the rigidity of the matrix thanks to the rigidity of the spacer layers. The matrix according to any embodiment of the invention can be compressed by any method known to the person skilled in the art. The size of the compressed matrix is reduced by maximum 20%, preferably maximum 15%, more preferably maximum 10% compared to the size of the non-compressed matrix.

In an embodiment, one surface of at least one spacer layer or section is at least partially free from coverage by any cell immobilization layers or other layer or section. The non-covered layer section or layer is designed to be positioned in contact with the inner wall of any bioreactor. This design allows preventing plunger effect inside the bioreactor.

In an alternative embodiment of the current invention, the matrix assembly is comprised of a configuration of one or more cell immobilization layers as described above forming an immobilization section and one or more spacer layers as described above forming a spacer section, positioned adjacent to (e.g. above and/or under) said cell immobilization layers. Optionally, the layering may be repeated to form an alternated, stacked configuration of one or more cell immobilization layers and one or more spacer layers. Said resulting configuration is subsequently spiral- or concentrically wound along an axis or core. The thickness of the spacer section may be between 0.1 mm and 5 mm, more preferably between 0.2 mm and 1 mm, whereas the thickness of the immobilization section may be between 0.1 and 5 mm. The ratio of thickness of the immobilization section over the thickness of the spacer section is preferably between 1:2 to 2:1, most preferably 1:1. While the amount of layers to achieve this may vary based on the characteristics of the layers used and thus freely chosen as described above, it was found that a good result was achieved when two immobilization layers are used and one spacer layer. The thickness of the spacer and immobilization layers is between 0.05 mm and 3 mm, more preferably between 0.1 and 2 mm or between 0.1 and 1 mm. While the material of the immobilization and spacer layer should not be construed as limitative, the immobilization layer is preferably made from a woven or nonwoven fabric or material as described above for the other embodiments. Said spacer layer may also be formed of a woven or nonwoven material and may include a mesh structure.

By preference, the outer layer of the assembly, being the side facing the wall of the bioreactor when placed within the bioreactor will be a spacer layer. This prevents cell growth against the wall of the reactor. Such bioreactors may be heated and cell growth in this area could compromise cell yield and/or quality. In a further embodiment, several spacer layers are provided at the outer border of the assembly, again to ensure good insulation. In another or further embodiment, an insulation layer which is made of another material than the spacer layer is provided.

The assembly of the matrix is simple and repeatable compared to those of the prior art. The invention further offers scalable matrixes by offering the possibility of easily producing matrixes having specific dimensions and/or cells growth surface. The scalability of the assembly/matrix of the invention has no impact on the homogeneity and/or the quality of the culture medium flow provided.

In another aspect, the present invention provides for the use of the assembly/matrix according to any embodiment described above for growing cells.

In another aspect, the present invention provides a bioreactor comprising an assembly or matrix according to any embodiment described above. The bioreactor might comprise more than one assembly or matrix. In a further embodiment, the assembly/matrix and/or the bioreactor comprising said matrix are single use. The assembly/matrix can be positioned vertically or horizontally in the bioreactor.

Preferably, the assembly/matrix represents at least 10%, at least 20%, at least 30%, at least 40% or at least 50% of the bioreactor inner space. Said matrix represents at most 100%, at most 90%, at most 80%, at most 70% or at most 60% of the bioreactor inner space.

The bioreactor can be any type of bioreactor known to the person skilled in the art such as perfusion bioreactor, wave bioreactor, cylindrical bioreactor, rotating bioreactor, bag bioreactor, moving bed bioreactor, packed bed bioreactor, fibrous bioreactor, membrane bioreactor, batch bioreactor, or continuous bioreactor. The bioreactor can be of any shape and can be made from any material, for example, stainless steel, glass, or plastic.

It is supposed that the present invention is not restricted to any form of realization described previously and that some modifications can be added to the presented example without reappraisal of the appended claims.

Figures

Figure 1B:
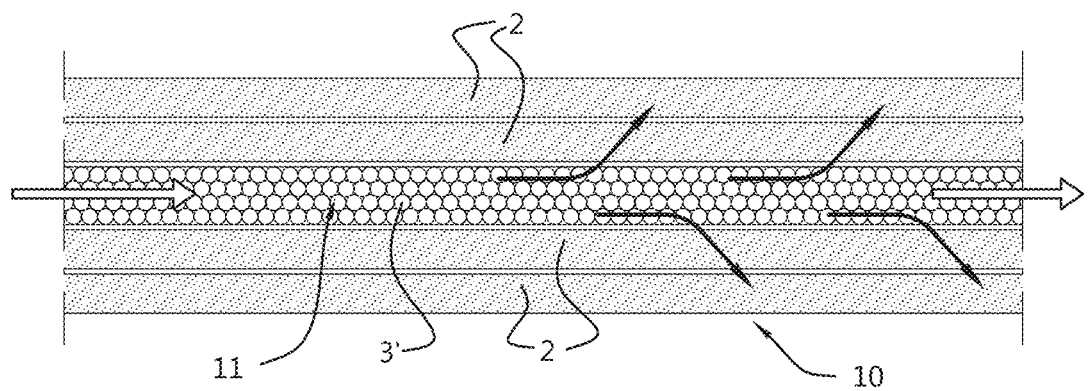

FIGS. 1A and 1B show cross-sectional views of portions of a matrix assembly according to two embodiments of the current invention. By providing one or more spacer layers 3 or 3' between one or more cell immobilization layers 2 (forming the immobilization section 10), turbulence (depicted with black arrows) and a random perpendicular flow (horizontal open arrows) is promoted. The assembly organises a fluid path which allows sufficient flow distribution when used within a fixed bed. By this design, liquid flow homogeneity is ensured and as a consequence, cells are equally homogenously distributed over the assembly. By providing a spacer creating a tortured, open path, cells and medium flow is allowed along the surface of both layers. The turbulence will push cells and medium deeper into the cell immobilization layers. Overall, the design promotes reproducibility and homogeneity when used for cell production.

FIG. 1A depicts an embodiment wherein the spacer section 11 is comprised of one or more spacer layers 3 which are made of a mesh fabric. Examples of possible mesh fabrics which can be used for this purpose are shown in FIGS. 4A to 4D, showing various forms of openings.

FIG. 1B depicts an alternative embodiment wherein the spacer section is made of spherical or near-spherical objects such as beads.

Both the mesh structure and the beads are examples of structures or layers which providing a tortured, open path as described above.

FIGS. 2A to 2D show possible arrangements of the number of immobilization layers versus spacer layers which respectively make up the cell immobilizations section 10 and spacer section 11.

The thickness of each section corresponds to the sum of the thickness of the layers contained therein. In a one embodiment, the spacer section 11 comprises one spacer layer and the cell immobilization section 10 comprises two cell immobilization layers as shown in FIGS. 2A and 2B. In this configuration, at least one surface of each immobilization layer is in contact with one surface of the spacer layer. FIGS. 2C and 2D show alternative examples, wherein the spacer section 11 comprises one spacer layer and the immobilization section comprises three immobilization layers.

The spacer sections and the cell immobilization section might be of any shape and might have similar of different dimensions. The matrix can be formed by alternating the different sections thereby obtaining a three dimension (3D) matrix. Said matrix can have any geometrical shape such cylindrical, triangular, rectangular or any irregular 3D shape. The matrix can also have other shapes obtained by further shaping the 3D matrix such as rolling the 3D matrix to obtain a spiral.

Figure 3A:
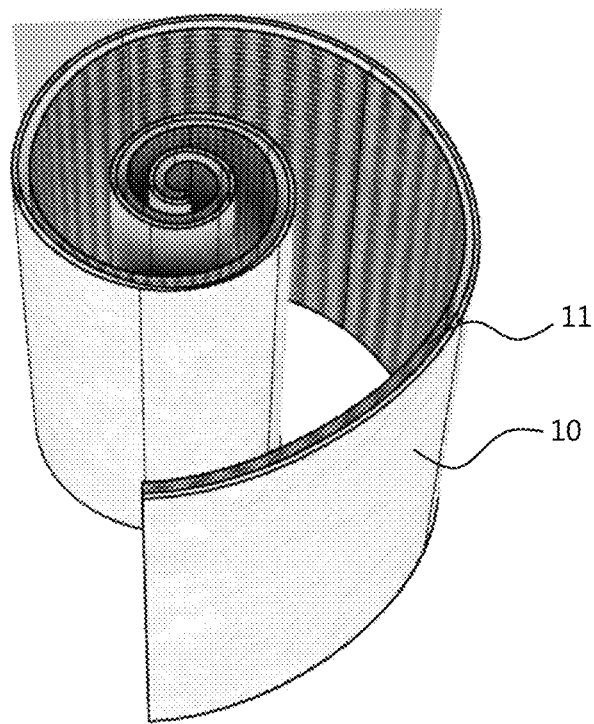
FIGS. 3A and 3B show a perspective and a top view of a matrix assembly partially rolled according to an embodiment of the invention; and an embodiment of an assembly in tightly packed configuration.
Figure 3B:
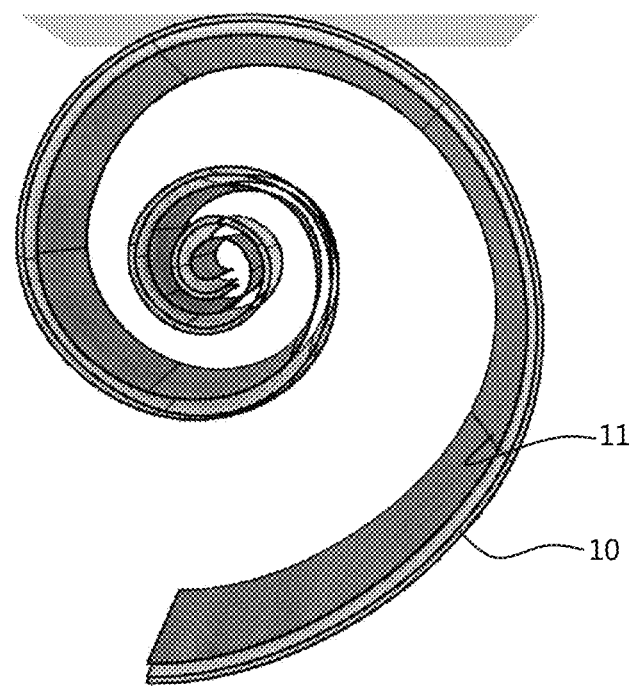

An example of a rolled matrix is shown in FIGS. 3A to 3B showing respectively a perspective view and a top view of the rolled matrix. These figures show a matrix or assembly which is "loosely" rolled to exemplify the spiral structure. It is to be understood that the degree of rolling the matrix is variable according to the use of the assembly and/or the wish of the user. The assembly or matrix will be tightly rolled to a structure such as the spiral structure shown in FIG. 3C.

Figure 3C:
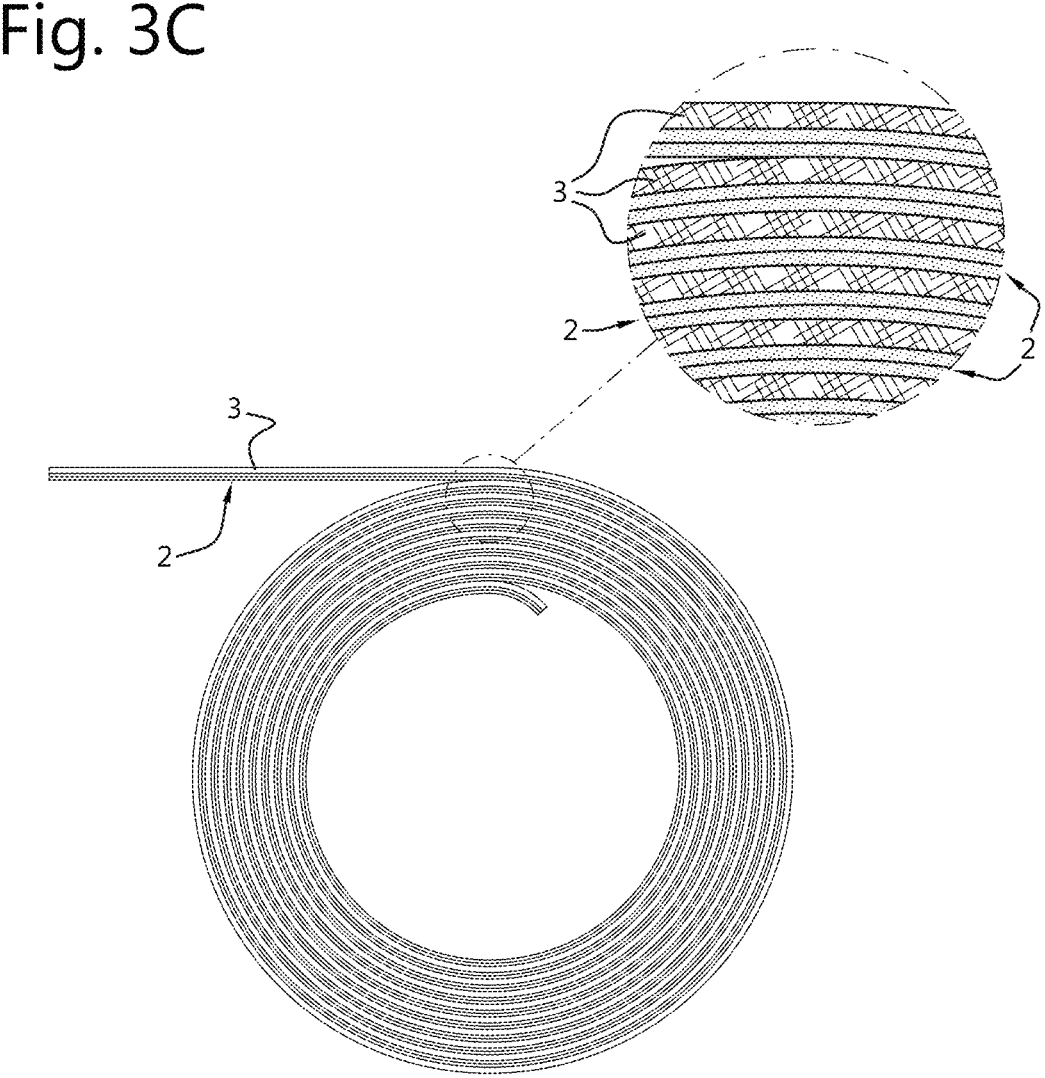
FIG. 3C shows a top view of a matrix fully rolled, according to an embodiment of the current invention.
Figure 4A:
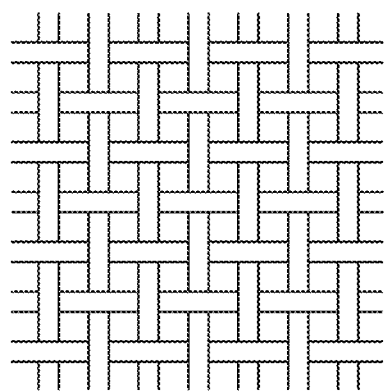
FIGS. 4A, 4B, 4C and 4D show examples of mesh spacer layer structures according to an embodiment of the current invention.
Figure 4B:
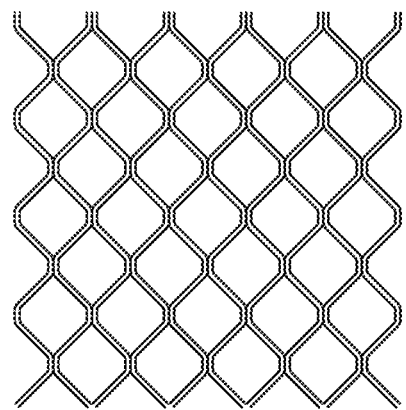
Figure 4C:
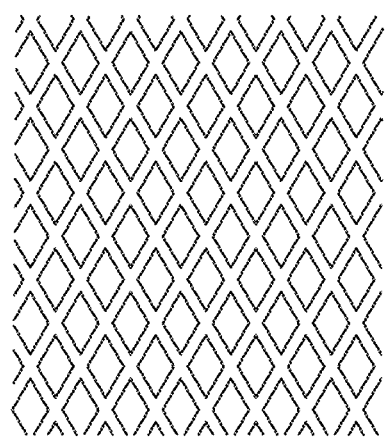
Figure 4D:
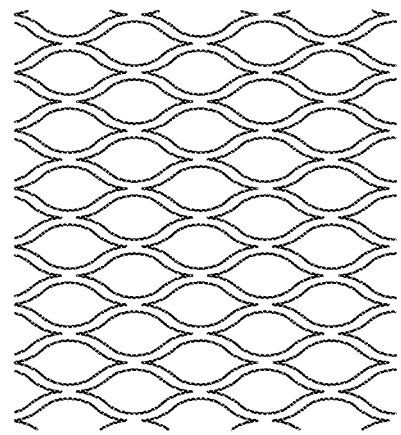

FIG. 3C shows an embodiment of the current invention, whereby one or more cell immobilization layers 2 are adjacent to one or more spacer layers 3 made from a mesh structure and whereby the layering may optionally be repeated several times to achieve a stacked configuration. Examples of mesh structures are given in FIGS. 4A to 4D (enlarged view). Preferably, the mesh structure included in spacer layers of the current invention forms a tortuous path for cells and fluid to flow when layered between two immobilization layers. Alternatively, other spacer structures can be used which form such tortuous paths. The embodiment shown in FIG. 3C is shown as subsequently spirally or concentrically rolled along an axis or core whereby all layers are firmly wound. The diameter of the core, the length and/or amount of the layers will ultimately define the size of the assembly or matrix. By preference, the thickness of the layers will be between 0.1 and 5 mm. In the embodiment shown in FIG. 3D, the thickness of the layers is between 0.25 and 0.7 mm, whereby two layers of cell immobilization layers are alternated by one spacer layer. By preference, the outer layer of the resulting spiral configuration will be one or more spacer layers. Alternatively, an insulating layer could be provided as outer layer, which differs from both the spacer and cell immobilization layer. The spacer layers are by preference a woven mesh fabric with mesh size between 0.05 mm and 5 mm. The cell immobilization layers are preferably a nonwoven fabric.

Figure 5:
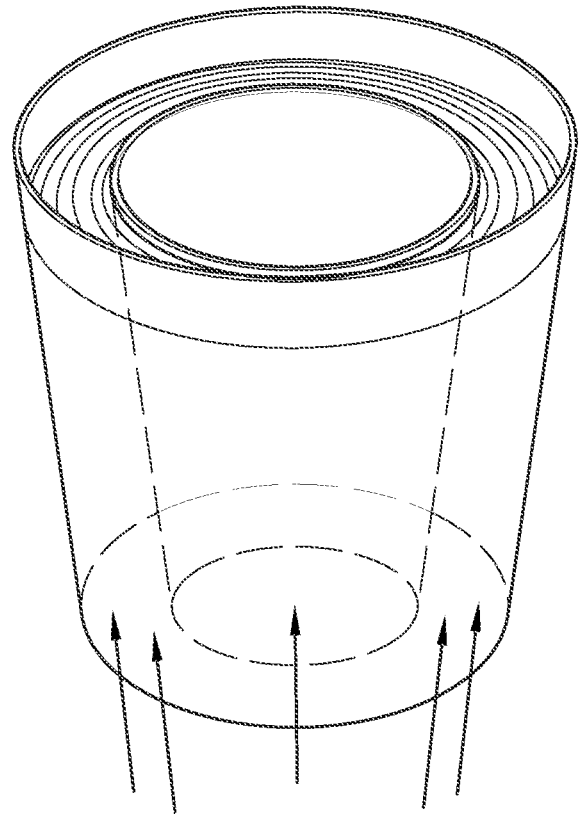
FIG. 5 shows a bioreactor chamber provided with a matrix assembly according to an embodiment of the current invention, in which fluid and cells flow axially along the surfaces of the spacer layers and immobilization layers between the top and bottom or bottom and top.
Figure 6:
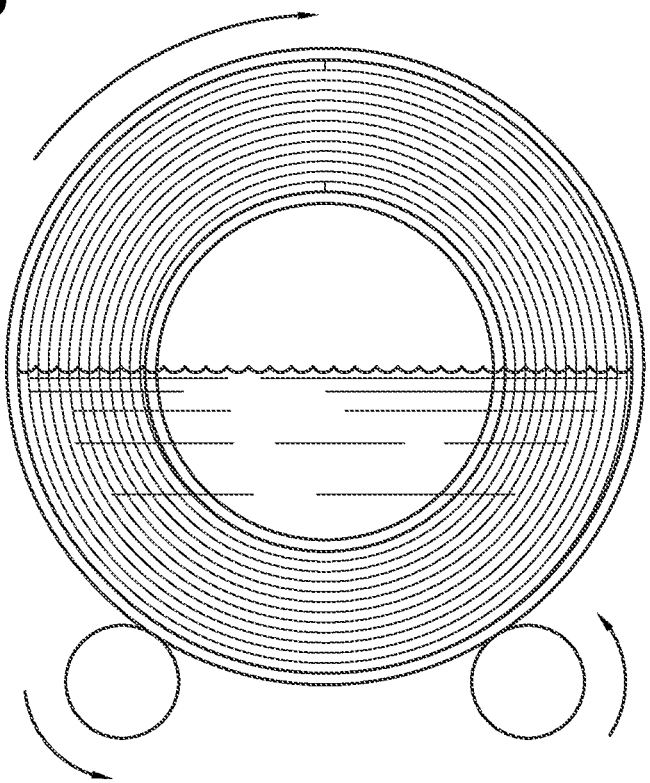
FIG. 6 shows a side view of a rotating bioreactor provided with a matrix assembly according to an embodiment of the current invention, rotating around its axis when in use.

FIGS. 5 and 6 show respectively a stationary bioreactor and a rotating bioreactor provided with a matrix assembly according to embodiments of the current invention.

In FIGS. 5 and 6, the matrix as shown in FIG. 3C is included in the bioreactor chambers. In both embodiments, the flow of cells and medium will be along the path created by the spacer layers.

In the embodiment as shown in FIG. 5, culture media and cells flow through the matrix assembly in the axial direction along the surface of the spacer and immobilization layers (from top to bottom or bottom to top).

FIG. 6 shows a rotating bioreactor whereby the matrix assembly is partially submerged in medium, and whereby the bioreactor and matrix are rotated along their axis. In this embodiment, the flow of medium and cells will be in the tangential direction along the surfaces of the spacer and immobilization layers (in the spiral path).

The invention claimed is:

1. A cell growth matrix assembly comprising a spiral configuration including a plurality of cell immobilization layers, each having a surface which allows cells to adhere and grow, and a plurality of spacer layers, each containing a tortuous path producing structure adjacent to each of said cell immobilization layers, and forming a channel allowing passage of cells and medium along the surface of the plurality of cell immobilization layers, the tortuous path producing structure of each spacer layer adapted to direct the cells into the one or more cell immobilization layers and adhere at a depth therein,
wherein said plurality of cell immobilization layers are made of a woven or nonwoven fabric;
wherein the cell growth matrix assembly includes an open central portion including a core about which the plurality of spacer layers and the plurality of cell immobilization layers are positioned;
wherein at least one of the plurality of spacer layers is unattached to an adjacent one of the plurality of cell immobilization layers;
wherein the cell growth matrix assembly comprises an innermost spacer layer and an outermost spacer layer; and
wherein a thickness ratio of at least one of the plurality of cell immobilization layers to at least one of the plurality of spacer layers is between 1:2 and 2:1.

2. The cell growth matrix assembly of claim 1, wherein a thickness ratio of at least one of the plurality of cell immobilization layers to at least one of the plurality of spacer layers is 2:1.

3. The cell growth matrix assembly of claim 1, wherein a thickness of each of the plurality of spacer layers is between 0.05 mm and 3 mm.

4. The cell growth matrix assembly of claim 1, wherein a thickness of each of the plurality of cell immobilization layers is between 0.05 mm and 3 mm.

5. Cell growth matrix assembly according to claim 1, wherein each spacer layer contains a mesh structure.

6. Cell growth matrix assembly according to claim 5, characterized in that the each spacer layer has a mesh size of between 0.05 mm to 5 mm.

7. Cell growth matrix assembly of claim 1, wherein at least two cell immobilization layers are in contact between at least two spacer layers of the plurality of spacer layers.

8. The cell growth matrix assembly of claim 1, wherein the plurality of cell immobilization layers are made of a biocompatible polymer selected from the group consisting of polyester, polyethylene, polypropylene, polyamide, plasma treated polyethylene, plasma treated polyester, plasma treated polypropylene or plasma treated polyamide.

9. The cell growth matrix assembly of claim 1, wherein the plurality of spacer layers are made of a biocompatible polymer selected from the group consisting of polyester, polyethylene, polypropylene, polyamide, plasma treated polyethylene, plasma treated polyester, plasma treated polypropylene or plasma treated polyamide.

10. The cell growth matrix assembly of claim 1, wherein the plurality of cell immobilization layers are hydrophilic.

11. The cell growth matrix assembly of claim 1, wherein the plurality of spacer layers are hydrophilic.

12. The cell growth matrix assembly of claim 1, wherein at least one surface of each immobilization layer is in contact with one surface of at least one spacer layer.

13. The cell growth matrix assembly of claim 1, wherein each spacer layer creates a channel allowing passage of cells and medium along a surface of an adjacent cell immobilization layer.

14. A bioreactor comprising a cell growth matrix assembly as described in claim 1.

15. The bioreactor of claim 14, further including a housing having therein an outer chamber for receiving the cell growth matrix assembly and an inner chamber located within the open central portion of the cell growth matrix assembly.

16. The bioreactor according to claim 14 having an inner space and wherein the cell growth matrix assembly represents at least 10% and at most 90% of said inner space.

17. The bioreactor according to claim 14, wherein the bioreactor and/or the cell growth matrix assembly are single use.

18. The bioreactor of claim 14, wherein the bioreactor is adapted to cause flow through the matrix assembly in an axial direction from bottom to top.

19. The bioreactor of claim 14, wherein the bioreactor is adapted to cause flow through the matrix assembly in an axial direction from top to bottom.

* * * * *

UNITED STATES PATENT AND TRADEMARK OFFICE
CERTIFICATE OF CORRECTION

| | | |
|---|---|---|
| PATENT NO. | : 10,876,090 B2 | Page 1 of 1 |
| APPLICATION NO. | : 15/938800 | |
| DATED | : December 29, 2020 | |
| INVENTOR(S) | : José Castillo et al. | |

It is certified that error appears in the above-identified patent and that said Letters Patent is hereby corrected as shown below:

In the Claims

Column 11, Claim 6, Line 4 - please delete "the"

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*